US010118049B2

(12) United States Patent
Matthews (10) Patent No.: US 10,118,049 B2
(45) Date of Patent: Nov. 6, 2018

(54) SYSTEMS AND METHODS FOR STIMULATION OF NEURONAL ACTIVITY

(75) Inventor: Charles Joseph Matthews, Raleigh, NC (US)

(73) Assignee: ARGUS NEUROOPTICS LLC, Raleigh, NC (US)

(*) Notice: Subject to any disclaimer, the term of this patent is extended or adjusted under 35 U.S.C. 154(b) by 401 days.

(21) Appl. No.: 13/392,271

(22) PCT Filed: Aug. 25, 2010

(86) PCT No.: PCT/US2010/046662
§ 371 (c)(1),
(2), (4) Date: Jun. 8, 2012

(87) PCT Pub. No.: WO2011/025830
PCT Pub. Date: Mar. 3, 2011

(65) Prior Publication Data
US 2012/0245659 A1 Sep. 27, 2012

Related U.S. Application Data

(60) Provisional application No. 61/236,748, filed on Aug. 25, 2009.

(51) Int. Cl.
*A61N 5/06* (2006.01)
*A61N 5/067* (2006.01)

(52) U.S. Cl.
CPC ......... *A61N 5/0601* (2013.01); *A61N 5/0622* (2013.01); *A61N 5/0618* (2013.01); *A61N 2005/0607* (2013.01); *A61N 2005/067* (2013.01); *A61N 2005/0643* (2013.01); *A61N 2005/0651* (2013.01); *A61N 2005/0659* (2013.01); *A61N 2005/0662* (2013.01)

(58) Field of Classification Search
CPC ............ A61N 5/062; A61N 2005/0652; A61N 5/0601; A61N 2005/067; A61N 5/0616; A61N 2005/0644
USPC ..................................................... 607/88, 89
See application file for complete search history.

(56) References Cited

U.S. PATENT DOCUMENTS

| 5,514,168 A | 5/1996 | Friedman | |
| 6,450,170 B1* | 9/2002 | Friedman | A61N 5/0603 128/898 |
| 6,491,940 B1* | 12/2002 | Levin | A61K 31/445 424/434 |
| 6,526,318 B1 | 2/2003 | Ansarinia | |

(Continued)

OTHER PUBLICATIONS

Definition of Insert. Merriam-Webster Dictionary, retrieved on Jun. 7, 2016; Retrieved from the internet:<http://www.merriam-webster.com/dictionary/insert>.*

(Continued)

*Primary Examiner* — Gary Jackson
*Assistant Examiner* — Sebastian X Lukjan
(74) *Attorney, Agent, or Firm* — Mintz Levin Cohn Ferris Glovsky and Popeo, P.C.

(57) ABSTRACT

Systems and methods for stimulating a neuronal cell in the head of a patient in need of such stimulation are disclosed. The method includes positioning a light source proximal to the neuronal cell to be stimulated and pulsing the light from the light source to stimulate the neuronal cell for a predetermined period of time to achieve the desired effect.

32 Claims, 5 Drawing Sheets

(56) References Cited

U.S. PATENT DOCUMENTS

| | | | |
|---|---|---|---|
| 9,180,308 B1* | 11/2015 | Frost | A61N 5/0622 |
| 2004/0030368 A1* | 2/2004 | Kemeny | A61N 5/0603 |
| | | | 607/88 |
| 2005/0107853 A1* | 5/2005 | Krespi | A61B 18/18 |
| | | | 607/89 |
| 2005/0154419 A1* | 7/2005 | Whitehurst et al. | 607/3 |
| 2006/0167531 A1* | 7/2006 | Gertner | A61N 5/0603 |
| | | | 607/86 |
| 2006/0276854 A1* | 12/2006 | Shalev et al. | 607/45 |
| 2006/0287695 A1* | 12/2006 | DiMauro et al. | 607/88 |
| 2007/0219600 A1* | 9/2007 | Gertner et al. | 607/88 |
| 2008/0033512 A1 | 2/2008 | Yu | |
| 2008/0077198 A1* | 3/2008 | Webb et al. | 607/88 |
| 2008/0125836 A1* | 5/2008 | Streeter et al. | 607/89 |
| 2008/0269847 A1 | 10/2008 | Nemenov | |
| 2009/0137923 A1 | 5/2009 | Suffin et al. | |
| 2009/0163982 A1 | 6/2009 | Decharms | |
| 2009/0299236 A1* | 12/2009 | Pryor | A61H 15/0092 |
| | | | 601/18 |

OTHER PUBLICATIONS

Definition of Surgery. Merriam-Webster Dictionary, retrieved on Jun. 7, 2016; Retrieved from the internet: <http://www.merriam-webster.com/dictionary/surgery>.*

International Search Report for Application No. PCT/US2010/046662 dated Oct. 13, 2010.

International Preliminary Report on Patentability and Written Opinion for International Application No. PCT/US2010/046662 dated Oct. 13, 2010.

* cited by examiner

SYSTEMS AND METHODS FOR STIMULATION OF NEURONAL ACTIVITY

CROSS-REFERENCE TO RELATED APPLICATIONS

The present application is a 35 U.S.C. § 371 national stage entry of PCT/US2010/046662, which has an international filing date of Aug. 25, 2010 and claims priority to U.S. Provisional Patent Application Ser. No. 61/236,748 to Matthews, filed on Aug. 25, 2009, entitled "Method of Stimulation of Neutronal Activity," and incorporates their disclosures herein by reference in their entireties.

COPYRIGHT NOTICE

A portion of the disclosure of this patent application contains material that is subject to copyright protection. The copyright owner has no objection to the reproduction by anyone of the patent document or the patent disclosure as it appears in the United States Patent and Trademark Office patent files or records, but otherwise reserves all copyright rights whatsoever.

BACKGROUND OF THE INVENTION

Field of the Invention

Some embodiments of the present application generally relate to stimulation of nerves with light. In particular, some embodiments of the present invention relate to nerve stimulation that affects nerve function(s) using light by inserting a light source intra-nasally until a desired position is reached and pulsing the light to quench, kindle or affect information transmission or the like of the desired nerve.

Background

Pain and other conditions associated with neuronal cells of the head are well known. One of the most common conditions associated with head neurons is the headache such as the migraine headache. Treatment of migraines has fallen into a number of different approach categories. Preventative treatment of migraines with medications has been extensively investigated. Typical medicinal treatments include antidepressants, anticonvulsants and antihypertensives. There have only been a few FDA approved medications for the prevention of migraines and all involve considerably serious side effects with their use. Treatment options for ongoing symptomatic pain have included opiate type drugs, caffeine, as well as most other types of anti-inflammatory drugs.

It has been estimated that there are more than 10 million people in the United States alone who either have an incomplete control of their migraines or have significant medicinal side effects from using current migraine medicines.

Because of the side effects associated with chemical treatments of these conditions, other conventional ways of the treatment of pain or neuronal related conditions have been developed. Examples of such conventional ways include U.S. Pat. Nos. 5,514,168 and 6,450,170 both to Friedman, which discuss treatment of migraines using a pulsed light laser. The laser is applied to areas of intra-oral maxillary tenderness. A probe tip is placed in the mouth of the subject and positioned proximal to the tender area in the mouth. According to Friedman, until tenderness is detected, no treatment can occur.

Another illustration of conventional ways of treating migranes includes U.S. Pat. No. 6,526,318 to Ansarinia, which relates to simulation of the sphenopalatine ganglia, sphenopalatine nerve or vidian nerve by positioning an electrode on or proximate to these nerves and applying an electrical signal to treat an array of conditions associated with facial and head neurons.

Other conventional methods for treating neuronal-related head conditions include acupuncture, biofeedback treatment and chiropractic adjustments. While in some cases these approaches show some limited use, they all involve either very expensive or time consuming treatments and only produce limited results.

A wide array of medical conditions and associated pain that occur in addition to the various types of migraine and other headaches are all connected to neuronal activity in the head. In addition to the pain, other conditions include movement disorders, epilepsy, cerebrovascular diseases, autoimmune diseases, sleep disorders, autonomic disorders, urinary bladder disorders, subnormal metabolic states, disorders of the musculature system and neuropsychiatric disorders to name a few. Mitigation or treatment of all these neuronal-connected conditions are still difficult and expensive in order to be successfully treated.

Thus, there is a need to provide effective and relatively inexpensive methods and systems for treatment of migraines and other types of headaches through stimulation that affects nerve function(s). Further, there is a need for methods and systems for treating pain and disorders associated with neuronal cells of the head, central nervous system, peripheral ganglia and nerves, etc. without the problems, side effects, or associated costs of prior treatment methods.

SUMMARY OF THE INVENTION

In some embodiments, the present invention relates to positioning of a light source within the therapeutic window proximal (including on) a neuronal cell to be treated by passing the light source into the nasal cavity to affect the neuronal function by stimulating the neuron. In some embodiments, the light source can be a GaAlAs laser operating in a near-infrared spectrum in the wavelength range of approximately 300 nanometers ("nm") to approximately 1200 nm. In some embodiments, the light source can have a wavelength of approximately 830 nm.

In some embodiments, the present invention relates to a method for stimulating a neuronal cell in the head of a patient in need of such stimulation. The method includes positioning a visible light source in the nasal cavity proximal to the neuronal cell and pulsing the light from the light source in a manner that to stimulates the neuronal cell for a predetermined period of time to achieve the desired effect.

In some embodiments, the positioning includes placing the light source in a nasal cavity of the patient. Further, the light source can be configured to generate light having a wavelength within a predetermined therapeutic range of wavelengths. The predetermined therapeutic range of wavelengths is from approximately 300 nanometers to 1200 nanometers.

In some embodiments, the light can be positioned for transmucosal stimulation. The light can also be positioned for transcranial stimulation.

In some embodiments, the light source can be a pulse laser. The laser can be a pulse laser. Further, the light source can include Ar laser, HeNe laser, and GaAlAs laser. In alternate embodiments, the light source is an LED.

In some embodiments, the pulsing can be done in a manner that quenches the neuron. Alternatively, the pulsing can be done in a manner that kindles the neuron. The pulsing can also be done in a manner that affects homeostatic information transmission.

In some embodiments, the stimulation is done to treat one or more of the conditions including, but not limited to, migraine, migraine headaches with aura, migraine headaches without aura, menstrual migraines, migraine variants, atypical migraines, complicated migraines, hemiplegic migraines, transformed migraines, chronic daily migraines, episodic tension headaches, chronic tension headaches, analgesic rebound headaches, episodic cluster headaches, chronic cluster headaches, cluster variants, chronic paroxysmal hemicranias, hemicrania continual, post traumatic headache, post traumatic neck pain, post herpetic neuralgia involving the head or face, pain from spine fracture secondary to osteoporosis, arthritis pain in the spine, headache related to cerebrovascular disease and stroke, headache due to vascular disorder, reflex sympathetic dystrophy, cervicalgia, glossodynia, carotidynia, cricoidynia, otalgia due to middle ear lesion, gastric pain, sciatica, maxillary neuralgia, laryngeal pain, myalgia of neck muscles, trigeminal neuralgia, post-lumbar puncture headache, low cerebra spinal fluid pressure headache, temporomandibular joint disorder, atypical facial pain, ciliary neuralgia, paratrigeminal neuralgia, petrosal neuralgia, Eagle's syndrome, idiopathic intracranial hypertension, orofacial pain, myofascial pain syndrome involving the head, neck and shoulder, chronic migraneous neuralgia, cervical headache, paratrigeminal paralysis, sphenopalatine ganglion neuralgia, carotidynia, Vidian neuralgia and causalgia. It can also be done to treat one or more of the following conditions: a movement disorder resulting from Parkinson's disease, cerebropalsy, dystonia, essential tremor and hemifacial spasms. The stimulation can be done to treat epilepsy. Further, the stimulation can be done to treat one or more of the following conditions: a cerebro vascular disease resulting from one or more medical conditions comprising vascular diseases affecting the carotid bulb including hypertension, carotid plaques and stenosis, aneurysms, strokes, and cerebral hemorrhage.

In some embodiments, the treatment can be done to treat one or more of autoimmune diseases resulting from multiple sclerosis, autonomic disorders resulting from one or more of gastrointestinal disorders, urinary bladder disorders, abnormal metabolic states, disorders of the muscular system, and neuropsychiatric disorders wherein the disorder is controlled by one or more neurons in the head.

In some embodiments, the light is positioned proximal to one or more of the sphenopalatine ganglia, sphenopalatine nerves or the vidian nerves, the extracranial nerves of the body including the carotid baroreceptors and carotid sinus, the ganglia of the face and neck, the stellate ganglia, the vagus nerve, the phrenic nerves, and splanchnic nerves, and the intracranial and spinal neurons of the central nervous system.

The present invention also contemplates use of multiple light sources. Specifically, there can be at least one light source positioned in each nostril of the patient. The present invention's system can also include an extension to transfer light from the light source to the desired location. The extension can be a fiber optic cable. The patient can wear the light source. The patient can be human or mammal.

In some embodiments, a controller can be configured to regulate an output of the light source based on a computer-generated algorithm. The computer generated algorithm can be selected from a group consisting of: a predetermined algorithm and an algorithm based on a biofeedback information from at least one biological sensor measuring at least one characteristic of the patient. The controller is further configured to control output of the light source based on an evoked responses, such as a trigeminal nerve evoked response, of the patient or an electroencephalogram. At least one scalp electrode coupled to the patient can be configured to record at least one characteristic of the patient to generate the electroencephalogram for analysis by the controller. The controller is configured to average data received from the electroencephalogram to producing a somatosensory evoked potential and determine when a sphenopalatine ganglion block has been completed. The evoked response includes a change in a trigeminal nerve evoked potential. The controller can be further configured to automatically stop the stimulation of the neural cell when the sphenopalatine ganglion block is completed. Using electroencephalogram, the controller is configured to monitor stimulation of neurons of a vagus nerve in the neck of the patient to prevent epileptic seizures. The controller is configured to generate a stimulus upon detection of epileptic discharges. The controller can be also configured to monitor blood pressure while neurons of the carotid sinus of the patient are being stimulated and regulate the stimulation in order to control blood pressure.

In some embodiments, the light source is configured to be directed at the nerves controlling output or function of an endocrine gland of the patient, wherein the endocrine gland is selected from a group consisting of pituitary gland, thyroid gland, or nerves subserving the ovaries or testicles or reproductive organs, or of the splanchnic ganglia and nerves that subserve digestion. The light source can be directed at neurons or nerves affecting output or function of the heart of the patient.

In some embodiments, the present invention relates to a system for stimulating a neuronal cell in the head of a patient in need of such stimulation. The system includes a light source coupled to a controller, wherein the controller is configured to control operation of the light source. The light source is configured to be positioned proximal to the neuronal cell of the patient to be stimulated. The controller is configured to pulse the light from the light source to stimulate the neuronal cell for a predetermined period of time to achieve the desired effect.

The details of one or more variations of the subject matter described herein are set forth in the accompanying drawings and the description below. Other features and advantages of the subject matter described herein will be apparent from the description and drawings, and from the claims.

BRIEF DESCRIPTION OF THE DRAWINGS

The accompanying drawings, which are incorporated in and constitute a part of this specification, show certain aspects of the subject matter disclosed herein and, together with the description, help explain some of the principles associated with the disclosed implementations. In the drawings, FIG. 1 schematically illustrates a lateral view of the skull showing the position of several nerves such as the Sphenopalatine ganglion.

DETAILED DESCRIPTION OF THE INVENTION

While the present invention may be susceptible to embodiments in many different forms, there is shown in the drawings and will herein be described in detail exemplary embodiments, with the understanding that the present application's disclosure of such embodiments is to be considered as an example of the principles and not intended to limit the invention to the specific embodiments shown and described. In the description below, like reference numerals are used to describe the same, similar or corresponding parts in the several views of the drawings. This detailed description defines the meaning of the terms used herein and specifically describes embodiments in order for those skilled in the art to practice the invention.

The terms "a" or "an", as used herein, are defined as one or as more than one. The term "plurality", as used herein, is defined as two or as more than two. The term "another", as used herein, is defined as at least a second or more. The terms "including" and/or "having", as used herein, are defined as comprising (i.e., open language). The term "coupled", as used herein, is defined as connected, although not necessarily directly, and not necessarily mechanically.

Reference throughout this document to "some embodiments", "one embodiment", "certain embodiments", and "an embodiment" or similar terms means that a particular feature, structure, or characteristic described in connection with the embodiment is included in at least one embodiment of the present invention. Thus, the appearances of such phrases or in various places throughout this specification are not necessarily all referring to the same embodiment. Furthermore, the particular features, structures, or characteristics may be combined in any suitable manner in one or more embodiments without limitation.

The term "or" as used herein is to be interpreted as an inclusive or meaning any one or any combination. Therefore, "A, B or C" means any of the following: "A; B; C; A and B; A and C; B and C; A, B and C". An exception to this definition will occur only when a combination of elements, functions, steps or acts are in some way inherently mutually exclusive.

The drawings featured in the figures are provided for the purposes of illustrating some embodiments of the present invention, and are not to be considered as limitation thereto. Term "means" preceding a present participle of an operation indicates a desired function for which there is one or more embodiments, i.e., one or more methods, devices, or apparatuses for achieving the desired function and that one skilled in the art could select from these or their equivalent in view of the disclosure herein and use of the term "means" is not intended to be limiting.

As used herein the term "stimulating" refers to causing a neuron or group of neurons such as a ganglia to be affected, i.e., change a property of the neuron function. For example, the neuron could be affected in its transformation of information (e.g., homeostatic information transmission rates), or it could either quench (either reduce or stop activity altogether) or kindle (activate or increase in activity). Depending on the condition to be treated, one having ordinary skill in the relevant art will be able to determine if and/or how a particular neuron needs to be stimulated to achieve the desired treatment effect. For example, it is known that either quenching or kindling of neurons in the head, central nervous system, and peripheral ganglia and nerves can suppress or prevent a host of disorders including pain, movement disorders, epilepsy, cerebrovascular diseases, autoimmune diseases, sleep disorders, autonomic disorders, urinary bladder disorders, abnormal metabolic states, disorders of the muscular system and neuropsychiatric disorders in a mammal or human patient (hereinafter, referred to as a "patient") Accordingly, as can be understood by one having ordinary skill in the relevant art, someone in need of such stimulation would be someone suffering from one or more of the above disorders or conditions or the like.

As used herein the phrase "light source" refers to a device configured to produce light within a predetermined therapeutic window, in which, the produced light is neither ionizing nor thermocoagulating. In some embodiments, the light source can produce light that is approximately in an infrared range to ultraviolet range. In some embodiments, the produced light can have a wavelength in the range of approximately 300 nm to approximately 1200 nm. Some embodiments of the present invention can be configured to produce light within the predetermined therapeutic window having wavelengths that are shorter or longer than the above-referenced wavelength ranges. The light produced by the light source can be pulsed or modulated in a way to prevent occurrence of any significant clinical damage to the surrounding tissue. In some embodiments, the produced light can be characterized by generating a low enough heat to not cause tissue damage. While discomfort or the like could occur, the controlling factor relates to damage of tissue especially the nerves being treated. While one having ordinary skill in the relevant art could chose light sources that meet the above criteria, two such sources can be light lasers and LEDs (light emitting diodes). In addition, the light source can be continuous wave or pulsed at the rates as discussed in the present application.

Laser light has unique properties that enable transmission of light to a narrowly defined area. The effects of laser light transmission are governed by tissue optical and thermal properties and laser variables, contact or non contact use, focus, output power (in milli-Watts ("mW")), exposure time, and number of exposures. The following discussion is a brief overview of various types of lasers that are currently available for use in various fields, including medicine.

One example of a laser includes a Helium-Neon ("HeNe") laser that can be configured to emit light at a wavelength of 633 nm and is probably one of the most commonly available lasers used in medicine. A low powered HeNe laser can be a tube filled with helium and neon. When the mixture is stimulated electrically, a beam of light in the visible spectrum is emitted. This type of laser can transmit low levels of light using fiber optic cables, such as quartz fibers.

Other examples of lasers include Argon ("Ar") lasers that operate at approximately 488 nm, are well known, and can be used for certain types of surgery. They can be outfitted with fiber optic extensions. Further examples includes Gallium arsenide ("GaAs") and gallium aluminum arsenide ("GaAlAs"), which are types of semiconductor lasers which emit a wavelength in the 850 nm range or near infrared band of the spectrum. In these lasers, the diode can be operated through a low powered electronic circuit utilizing internal optical feedback to maintain a constant power output.

In some embodiments, a coherent laser light can be focused by lenses into a glass-optic assembly, which is attached via a connector to the laser source for convenience and interchangeability. Use of a fiber-optic structure (or other similar extension) allows application of the laser light at a desired location proximate to the neuronal cell such that it is easily maneuverable and easy to position and does not inadvertently stimulate an undesired neuron. These types of lasers are well known and their use is within one's ordinary skill in the relevant art. An ability to select a power that does not damage tissue is also within one's ordinary skill in the relevant art.

In some embodiments, the light source can include an LED light. LED lights operate in a number of visible wavelengths, are relatively low power and, hence, do not generate a great deal of thermal energy. In addition, they can be used with a fiber optic head or extension so that the LED light source itself does not enter a nasal cavity of the patient and thus, can be narrowly focused like the laser. Their low cost of operation also makes them ideal for producing light for use in some embodiments of the present invention. As can be understood by one having ordinary skill in the relevant art, other light sources compatible with a fiber optic cable, besides lasers and LED lights can be used. In some embodiments, the present invention can be configured to include multiple tips for production of light, for example, two tips can be used—one for each nostril. This could be accomplished by using two separate light sources or by using two extensions, e.g., fiber optic cables, connected to a single light source.

As used herein "inserting in the nasal cavity" refers to the insertion of the tip of the light source (the light or the extension) into the left nostril, the right nostril or both (either alternatively or with two or more lights). The insertion can include insertion of the light itself or the extension, such as a fiber optic cable or other means for transmitting the light from the source to the tip entering the nasal cavity. The tip of the light source is then positioned proximate to the neuronal cell to be stimulated. "Proximate" means either touching the mucosal tissue over the neuron, touching the neuron itself or in a position sufficiently close to the neuron to have the desired effect of stimulating the cell. When positioned on or near mucosal tissue, the light is positioned for transmucosal stimulation. The light source may also be positioned and powered for stimulation of structures deeper than the sphnopalatine ganglion, such as the neurons of the brain, in which case it is considered a transcranial stimulation. transcranial Where transmucosal stimulation is used, the light source can be inserted into the nose. Transcranial stimulation may be performed with wavelengths and power transmission (measured in Watts) that penetrate deeper into intracranial structures without the need for surgical incision or suturing. For example, U.S. Pat. No. 6,526,318 relates to a surgical technique that uses of electrodes for entering the cranial area. It should be noted that focusing the light at a particular structure rather than a wide beam of light helps to prevent other neurons from being stimulated unnecessarily.

As used herein the term "pulsing" in order to stimulate the neuronal cell refers to having the light source turn on and off (in a form of a cycle) at a predetermined rate. If the light is pulsed at a slow rate, the neuron is allowed to recover before the next stimulation pulse and then it is kindled. This may vary from cell to cell. In some embodiments, if the frequency of pulses is about 1 CPS or less, it is sufficient to kindle neurons in the head. If on the other hand the frequency of the light pulse is greater than the recovery time of the cell, then the activity of the cell is quenched to some partial or incomplete degree. Other forms of stimulation such as transmission affects can be performed at various speeds. As can be understood by one having ordinary skill in the relevant art, pulse rates to achieve a desired stimulation effect can be readily determined. For example, most cells will quench at a frequency of 10-20 CPS or more. In some embodiments, a continuous pulsing can be used. In alternate embodiments, a measurable pulse can be used.

In order to determine the amount of time for treatment to achieve the desired effect, some embodiments of the present invention are configured to determine the type of light being used, the position of the light and a number of other factors as discussed in the present application. In some embodiments, a single treatment can be applied to a patient/patient during a predetermined period of time. In alternate embodiments, multiple treatments each having a predetermined application time can be applied, where a total application time of all treatments can be predetermined as well. In some exemplary embodiments, treatments can be about 1 to 10 minutes in length. Treatments can be repeated either in each nostril or both nostrils. Treatments can also be repeated on an as needed basis depending, for example, on the severity and type of disorder being treated, the type of light, and/or light source's exact positioning in the patient. As can be understood by one having ordinary skill in the relevant art, Times and frequencies of treatment can be determined based on the patient (e.g., physical condition, characteristics, etc.), condition being treated, characteristics of the light source (e.g., wavelength, LED, laser, type of laser/LED, etc.), and/or any other factors.

In some embodiments, the present invention relates to a method for treatment of a condition in a patient where the method is configured to utilize light stimulation of the sphenopalatine ganglion ("SPG", also called the pterygopalatine ganglion), the sphenopalatine nerve ("SPN", also called the pterygopalatine nerve), the nerve of the pterygoid canal, also termed the vidian nerve ("VN"), vagus nerve in the neck, stellate ganglion in the neck, baroreceptors in the carotid sinus, autonomic ganglia and dorsal roots exiting the spine, and/or all other central and peripheral nerves and ganglia using one or more light sources, for treatment of a number of medical conditions. Medical conditions which may be treated by the present invention's systems and methods include, but are not limited to: pain, movement disorders, epilepsy, cerebrovascular diseases, autoimmune diseases, sleep disorders, autonomic disorders, urinary bladder disorders, abnormal metabolic states, disorders of the muscular system, and neuropsychiatric disorders.

Pain treatable by the present invention's systems and methods may be caused by conditions including, but not limited to: migraine headaches, including migraine headaches with aura, migraine headaches without aura, menstrual migraines, migraine variants, atypical migraines, complicated migraines, hemiplegic migraines, transformed migraines, and chronic daily migraines; episodic tension headaches; chronic tension headaches; analgesic rebound headaches; episodic cluster headaches; chronic cluster headaches; cluster variants; chronic paroxysmal hemicrania; hemicrania continua; post-traumatic headache; post-traumatic neck pain; post-herpetic neuralgia involving the head or face; pain from spine fracture secondary to osteoporosis; arthritis pain in the spine, headache related to cerebrovascular disease and stroke; headache due to vascular disorder; reflex sympathetic dystrophy, cervicalgia (which may be due to various causes, including, but not limited to, muscular, discogenic, or degenerative, including arthritic, posturally related, or metastatic); glossodynia, carotidynia; cricoidynia; otalgia due to middle ear lesion; gastric pain; sciatica; maxillary neuralgia; laryngeal pain, myalgia of neck muscles; trigeminal neuralgia (sometimes also termed tic douloureux); post-lumbar puncture headache; low cerebrospinal fluid pressure headache; temporomandibular joint disorder; atypical facial pain; ciliary neuralgia; paratrigeminal neuralgia (sometimes also termed Raeder's syndrome); petrosal neuralgia; Eagle's syndrome; idiopathic intracranial hypertension; orofacial pain; myofascial pain syndrome involving the head, neck, and shoulder; chronic migraneous neuralgia, cervical headache; paratrigeminal paralysis; sphenopalatine ganglion neuralgia (sometimes also termed lower-half headache, lower facial neuralgia syndrome, Sluder's neuralgia, and Sluder's syndrome); carotidynia; Vidian neuralgia; and causalgia; or a combination of the above.

Movement disorders treatable by the present invention's systems and methods may be caused by conditions including, but not limited to: Parkinson's disease; cerebropalsy; dystonia; essential tremor; and hemifacial spasms. Epilepsy treatable by the inventive method may be, for example, generalized or partial. Cerebrovascular disease treatable by the present invention's systems and methods may be caused by conditions including, but not limited to: aneurysms, strokes, and cerebral hemorrhage. Autoimmune diseases treatable by the present invention's systems and methods include, but are not limited to, multiple sclerosis. Sleep disorders treatable by the inventive method may be caused by conditions including, but not limited to: sleep apnea and parasomnias. Autonomic disorders treatable by the present invention's systems and methods may be caused by conditions including, but not limited to: gastrointestinal disorders, including but not limited to gastrointestinal motility disorders, nausea, vomiting, diarrhea, chronic hiccups, gastroesphageal reflux disease, and hypersecretion of gastric acid; autonomic insufficiency; excessive epiphoresis; excessive rhinorrhea; and cardiovascular disorders including but not limited to cardiac dysrythmias and arrythmias, hypertension, and carotid sinus disease. Urinary bladder disorders treatable by the present invention's systems and methods may be caused by conditions including, but not limited to: spastic or flaccid bladder. Abnormal metabolic states treatable by the present invention's systems and methods may be caused by conditions including, but not limited to: diseases and/or functional disorders of the nerves subserving the pituitary gland, and endocrine system. Disorders of the muscular system treatable by the present invention's systems and methods include, but are not limited to, muscular dystrophy and spasms of the upper respiratory tract and face. Neuropsychiatric disorders treatable by the present invention's systems and methods may be caused by conditions including, but not limited to: depression, schizophrenia, bipolar disorder, obsessive-compulsive disorder, anxiety disorders, panic attacks, and/or phobias.

The present invention is configured to act to suppress or prevent these conditions by disrupting sensory signals transmission through the autonomic, peripheral, or central nervous system, including pain signals, as the signals traverse the SPG, or other central or peripheral nerves or ganglia. The abnormal regulation of pain pathways, which may be a feature of the conditions listed above, can cause excitation or a loss of inhibition of those pathways, resulting in an increased perception of pain. Direct light stimulation of the SPG, or other autonomic, peripheral, or central nervous system neurons, is configured to block the transmission of pain signals and stimulate inhibitory feedback of the pain pathways passing through the SPG, or other autonomic, peripheral, or central nervous system neurons, reducing or eliminating the pain experienced by the patient. Similarly, stimulation of the SPG, or other autonomic, peripheral, or central nervous system neurons can be configured to block the transmission of signals other than pain which can provoke or aggravate other undesirable sensations or conditions, such as nausea, bladder disorders, sleep disorders or abnormal metabolic states.

The autonomic system, which innervates pain pathways within the human body, includes two divisions: the sympathetic system and the parasympathetic system. The sympathetic and parasympathetic systems are antagonistic in their action, balancing the other system's effects within the body. The sympathetic system usually initiates activity within the body, preparing the body for action, while the parasympathetic system primarily counteracts the effects of the sympathetic system.

SPG, or other autonomic, peripheral, or central nervous system neurons structures are located on both sides of a patient's head. The inventive method may be applied to apply stimulus to the SPG, or other autonomic, peripheral, or central nervous system neurons on either or both sides of the patient's head through the nasal cavities.

Accordingly, the present invention is not limited to the above neuronal structures and other neurons within the head are also contemplated within the scope of the present invention using the same technique as for the above neurons. For example nerves such as supraorbital, nasociliary, zygomatotemporal, occipital, palatine or ganglia such as the ciliary and otic, as well as the neurons in the carotid bulb, the vagus nerve, the phrenic nerve, the brachial plexus, the stellate ganglion, and dorsal root nerves and ganglia of the spine.

Figure 1:
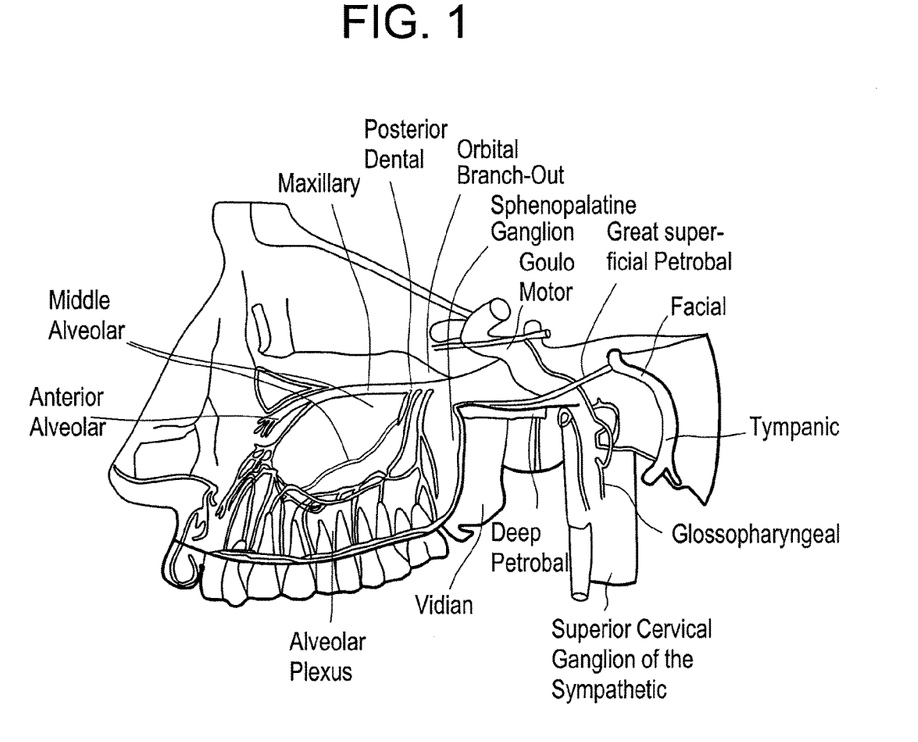
Figure 2:
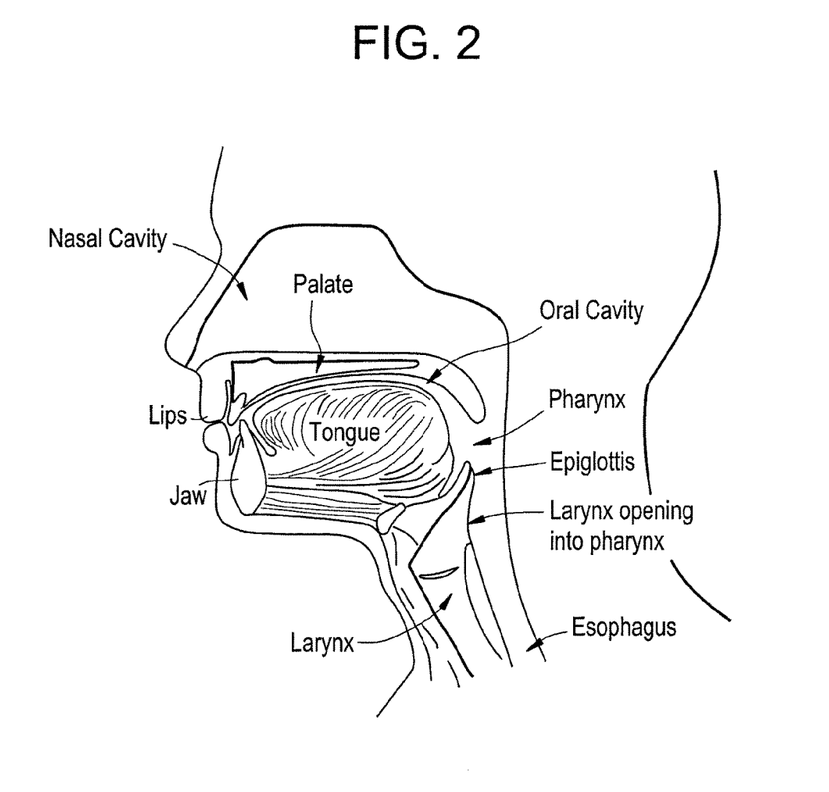
FIG. 2 schematically illustrates a lateral view of the skull showing the nasal cavity.
Figure 3:
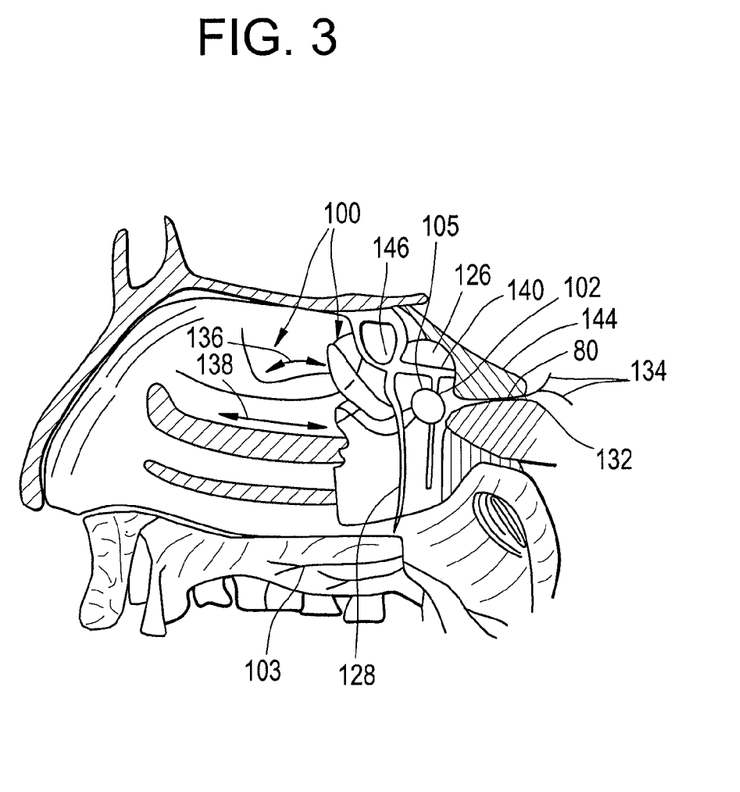
FIG. 3 schematically illustrates another view of the skull, according to some embodiments of the present invention.
Figure 5:
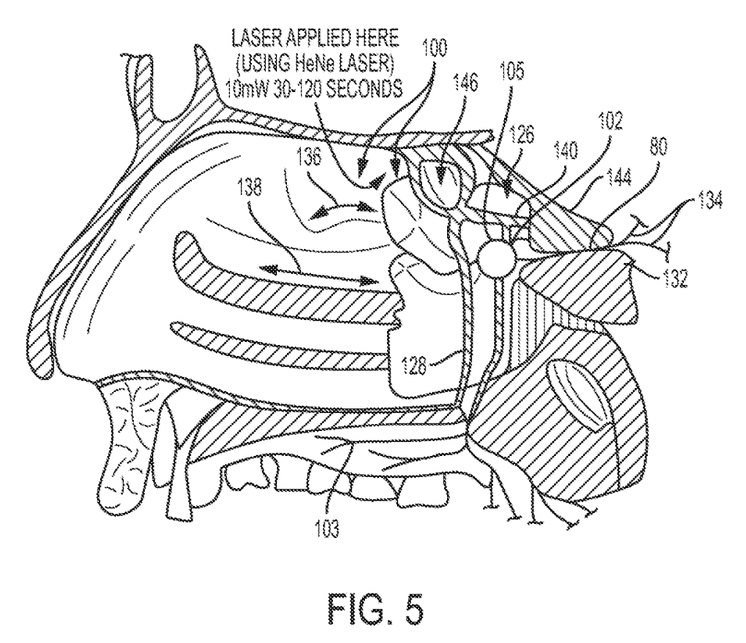
FIG. 5 is a schematic drawing showing an exemplary positioning of a HeNE probe in the nasal cavity, according to some embodiments.

FIGS. 1 and 2 schematically lateral views of the skull showing the position of several nerves such as the Sphenopalatine ganglion and the skull showing the nasal cavity, respectively. In some embodiments, as shown in FIG. 3, a light source is configured to be placed proximate to a neuronal cell to be stimulated for the purposes of treating any and/or all of the above discussed conditions or any other conditions. FIG. 3 (and FIG. 5, which corresponds to FIG. 3 of the U.S. Provisional Patent Appl. No. 61/236,748, to which the present application claims priority to and incorporates its contents herein by reference in their entireties) schematically illustrates an exemplary positioning of a HeNe probe in the nasal cavity, according to some embodiments of the present invention. FIG. 5 illustrates a location of application of a laser and exemplary application parameters (as shown by an arrow with words "Laser applied here (using HeNe laser), "10 mW" and "30-120 seconds"). FIG. 3 also illustrates various nerves in the skull, including Sphenopalatine ganglion 146, nerve of pterygoid canal 140, facial nerves 80 and 134, pharyngeal nerve 132, trigeminal nerve's 3 branches 102, 105, 126, anterior palatine nerve 103, middle palatine nerve 128, and nasal branches 136, 138. As can be understood by one having ordinary skill in the relevant art, other types of lasers can be used. The laser can be controlled using a controller (e.g., a computer having a central processing unit, a memory, a display, a keyboard, a mouse, and/or any other components). In some embodiments, the controller can be configured to regulate an output of the light source based on a computer-generated algorithm. The computer generated algorithm includes a predetermined algorithm or an algorithm based on a biofeedback information from at least one biological sensor measuring at least one characteristic of the patient. The sensor can be placed directly or indirectly on the patient and can measure patient's blood pressure, heart rate, neural response, and/or any other patient-related characteristic.

Figure 4:
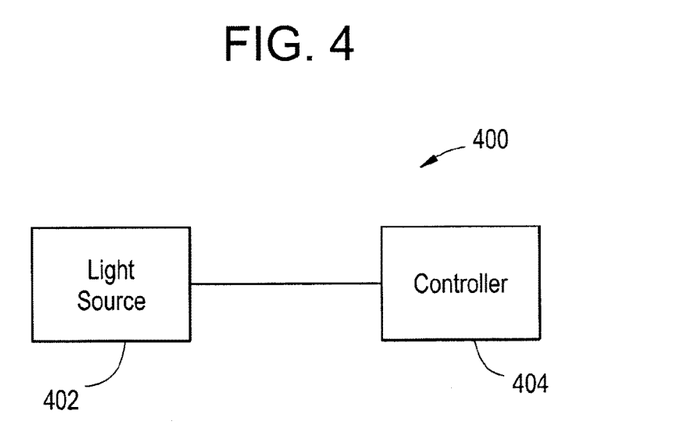
FIG. 4 is a block diagram illustrating an exemplary system for performing stimulation of neuronal activity.

FIG. 4 is a block diagram illustrating an exemplary system 400 for performing stimulation of neuronal activity, according to some embodiments of the present invention.

System 400 includes a light source 402 coupled to a controller 404. The light source 402 can be any type of laser operating within a predetermined range of wavelengths, as discussed above, an LED light source, or any other type of light source suitable for performing stimulation of the neuronal activity. The controller 404 can be configured to control stimulation of the neuronal activity by the light source 402. The controller 404 can include a central processing unit, a memory, a monitor, a keyboard, a mouse and/or any other component configured to perform various functions of the controller 404.

In some embodiments, the controller can be configured to control output of the light source based on an evoked responses of the patient or an electroencephalogram ("EEG"). In some embodiments, the evoked responses are the changes in the trigeminal nerve evoked potential. The EEG can be obtained using at least one scalp electrode coupled to the patient that records at least one characteristic of the patient. The EEG is analyzed by the controller. The controller can average the data received from the EEG to produce a somatosensory evoked potential and to determine when a sphenopalatine ganglion block has been completed. The controller can automatically stop the stimulation of the neural cell when the sphenopalatine ganglion block is completed or request user's input. Using the obtained EEG, the controller can also monitor stimulation of neurons of a vagus nerve in the neck of the patient to prevent epileptic seizures. To do so, the controller generates a stimulus upon detection of epileptic discharges.

In some embodiments, the controller is configured to monitor blood pressure while neurons of the carotid sinus of the patient are being stimulated. The controller can further be configured to regulate the stimulation in order to control blood pressure.

Examples

1. Cluster Headaches and Migraines

A series of individuals exhibiting the symptoms of a cluster headache or migraine headache were treated in this example. A probe from a 10 MW HeNe laser which was set to pulse at 20 CPS is inserted into the left open nare and threaded past the inferior turbinate. The light was engaged and directed at the mucosa overlying the sphenopalatine ganglion. The treatment was continued in each individual for a period of from about 3 to as much as 10 minutes. The process was then repeated on the opposite side to produce a treatment of the right sphenopalatine ganglion (a block). The presence of the block was demonstrated by reduction in pain experienced by each individual, cessation of nausea and headache symptoms such as sensitivity to light and sound. On average pain was reduced on a scale of 10 (worse) to 1 (no pain) from about an 8 to about a 1.

2. Sinusitis, Allergic Rhinitis and Common Cold Congestion

A series of individuals with either sinusitis, allergic rhinitis or congestion due to the common cold are treated in the manner of the above example except the probe is positioned to shine on the supraorbital nerves and/or nasociliary nerves above and medial to the eye, thereby causing a nerve block of the treated nerves. Individuals treated experience drainage of the sinuses and relief of pain.

Example embodiments of the methods and components of the present invention have been described herein. As noted elsewhere, these example embodiments have been described for illustrative purposes only, and are not limiting. Other embodiments are possible and are covered by the invention. Such embodiments will be apparent to persons skilled in the relevant art(s) based on the teachings contained herein. Thus, the breadth and scope of the present invention should not be limited by any of the above-described exemplary embodiments, but should be defined only in accordance with the following claims and their equivalents.

What is claimed:

1. A method of treating a symptom of a headache-related medical condition, including a headache and/or a pain from a headache-related condition, in a patient, the method comprising:
providing a controller coupled to a light source and capable of being configured to be coupled to at least one electrode, a signal from the at least one electrode is used for generation of an electroencephalogram;
positioning the light source proximal to a neuronal cell to be stimulated, wherein the light source is temporarily, without surgical intervention or suturing, placed in a nasal cavity of the patient, wherein proximate positioning includes at least one of the following: touching a mucosal tissue over the neuronal cell and touching the neuronal cell;
pulsing a light, using a predetermined frequency, a predetermined low power, and a wavelength of approximately 300 nanometers to approximately 1200 nanometers, from the light source, for a predetermined period of time or a period of time based on a feedback from at least one of the following: a trigeminal evoked response data, and an electroencephalogram data; the predetermined frequency includes at least one of the following: a range of 10 cycles per second (Hz) to 20 cycles per second (Hz), and a frequency of less than 1 cycle per second (Hz);
controlling, using the controller, an output of the light source based on at least one of the following in combination with a predetermined output of light: an evoked response of the patient, a trigeminal nerve evoked response, the electroencephalogram, and any combination thereof;
stimulating, using the pulsed light, the neuronal cell, to treat the headache-related medical condition, for a predetermined period of time to provide treatment of the symptom of the headache-related medical condition of the patient, the stimulating including changing at least one property of at least one function of the neuronal cell, wherein the changing of the at least one property includes at least one of the following: quenching the neuronal cell, kindling the neuronal cell, affecting homeostatic information transmission, and any combination thereof;
stopping the stimulating after a predetermined period of time or based on at least one of the following: the evoked response of the patient, the trigeminal nerve evoked response, the electroencephalogram, and any combination thereof.

2. The method according to claim 1, wherein the light source is positioned for transmucosal stimulation.

3. The method according to claim 1, wherein the light source is positioned for transcranial stimulation.

4. The method according to claim 1, wherein the light source is a laser.

5. The method according to claim 4, wherein the laser is a pulse laser.

6. The method according to claim 4, wherein the light source is selected from a group consisting of: Ar laser, HeNe laser, and GaAlAs laser.

7. The method according to claim 1, wherein the light source is an LED.

8. The method according to claim 1, wherein the symptom of the at least one condition includes one of the following: migraine, headaches with aura, migraine headaches without aura, menstrual migraines, migraine variants, atypical migraines, complicated migraines, hemiplegic migraines, transformed migraines, chronic daily migraines, episodic tension headaches, chronic tension headaches, analgesic rebound headaches, episodic cluster headaches, chronic cluster headaches, cluster variants, chronic paroxysmal hemicranias, hemicrania continual, post traumatic headache, post herpetic neuralgia involving the head or face, headache related to cerebrovascular disease and stroke, headache due to vascular disorder, cricoidynia, otalgia due to middle ear lesion, maxillary neuralgia, laryngeal pain, myalgia of neck muscles, trigeminal neuralgia, post-lumbar puncture headache, low cerebro spinal fluid pressure headache, temporomandibular joint disorder, atypical facial pain, ciliary neuralgia, paratrigeminal neuralgia, petrosal neuralgia, Eagle's syndrome, idiopathic intracranial hypertension, orofacial pain, myofascial pain syndrome involving the head, neck and shoulder, chronic migraneous neuralgia, cervical headache, paratrigeminal paralysis, sphenopalatine ganglion neuralgia, carotidynia, Vidian neuralgia and causalgia.

9. The method according to claim 1, wherein the light source is positioned proximal to one or more of the sphenopalatine ganglia, sphenopalatine nerves or the vidian nerves, the extracranial nerves of the body including the carotid baroreceptors and carotid sinus, the ganglia of the face and neck, the stellate ganglia, the vagus nerve, the phrenic nerves, and splanchnic nerves, and the intracranial and spinal neurons of the central nervous system.

10. The method according to claim 1, further comprising a plurality of light sources.

11. The method according to claim 10, wherein at least one light source in the plurality of light sources is positioned in each nostril of the patient.

12. The method according to claim 1, further comprising an extension coupled to the light source for transferring light from the light source to a desired location.

13. The method according to claim 12, wherein the extension is a fiber optic cable.

14. The method according to claim 1, wherein the light source is worn by the patient.

15. The method according to claim 1, wherein the patient is a human.

16. The method according to claim 1, wherein the controller averages data received from the electroencephalogram or a trigeminal nerve evoked potential measurement to determine when a sphenopalatine ganglion block has been completed;
wherein the evoked response includes a change in the trigeminal nerve evoked potential;
wherein the controller automatically stops the stimulation of the neuronal cell when the sphenopalatine ganglion block is completed.

17. The method according to claim 1, wherein the light generated by the light source is directed at neurons and/or nerves affecting output and/or function of the heart of the patient.

18. The method according to claim 4, wherein the laser is a low power laser.

19. The method according to claim 7, wherein the LED light source is a low power LED light source and operates using at least one visible wavelength.

20. The method according to claim 19, wherein at least one of the following: a fiber optic head and an extension, is configured to be coupled to the LED light source.

21. The method according to claim 19, wherein the LED light source is narrowly focused.

22. The method according to claim 1, wherein the light source is an LED laser.

23. The method according to claim 1, wherein the positioning further comprises
positioning the light source proximal and directed at the neuronal cell to be stimulated.

24. The method according to claim 23, further comprising focusing the pulsed light on the neuronal cell, thereby avoiding stimulating at least one other neuronal cell adjacent to the neuronal cell.

25. The method according to claim 1, wherein the controller determines the predetermined time based on at least one of the following: a type of light source, a position of the light source proximal to the neuronal cell, and at least one patient-specific factor.

26. The method according to claim 1, further comprising terminating the stimulating of the neuronal cell upon detecting a blocking condition in the neuronal cell.

27. A method of treating a symptom of a headache-related medical condition, including a headache and/or a pain from a headache-related condition, in a patient, comprising:
providing a controller coupled to a light source and capable of being configured to be coupled to at least one electrode, a signal from the at least one electrode is used for generation of an electroencephalogram;
temporarily placing the light source in a nasal cavity of the patient, wherein a tip of the light source is positioned proximate to a neuronal cell in a head of the patient, the light source being focused on a narrowly defined area, the narrowly defined area including the neuronal cell in a head of the patient, the proximate positioning includes at least one of the following: touching a mucosal tissue over the neuronal cell and touching the neuronal cell;
generating a pulsed light from the light source, using a predetermined frequency, a predetermined low power, and a wavelength of approximately 300 nanometers to approximately 1200 nanometers, to stimulate the neuronal cell, to treat the headache-related medical condition, for a predetermined period of time or a period of time based on a feedback from at least one of the following: a trigeminal evoked response data, and an electroencephalogram data; the predetermined frequency includes at least one of the following: a range of 10 cycles per second (Hz) to 20 cycles per second (Hz), and a frequency of less than 1 cycle per second (Hz); and
controlling, using a controller coupled to the light source, stimulation of the neuronal cell, thereby providing treatment of the symptom of the headache-related medical condition in the patient, the controller controls an output of the light source based on at least one of the following in combination with a predetermined output of light: an evoked response of the patient, a trigeminal nerve evoked response, the electroencephalogram, and any combination thereof;
wherein the stimulating includes changing at least one property of at least one function of the neuronal cell, wherein the changing of the at least one property includes at least one of the following: quenching the neuronal cell, kindling the neuronal cell, affecting homeostatic information transmission, and any combination thereof;
stopping the stimulating after a predetermined period of time or based on at least one of the following: the evoked response of the patient, the trigeminal nerve evoked response, the electroencephalogram, and any combination thereof.

28. A method of treating a symptom of a headache-related medical condition, including a headache and/or a pain from a headache-related condition, in a patient, comprising:
providing a controller coupled to a light source and capable of being configured to be coupled to at least one electrode, a signal from the at least one electrode is used for generation of an electroencephalogram;
temporarily placing the light source in a nasal cavity of the patient;
advancing the light source inside the nasal cavity to position the light source proximate to a neuronal cell to be stimulated, the proximate positioning includes at least one of the following: touching a mucosal tissue over the neuronal cell and touching the neuronal cell; and
pulsing, using a predetermined frequency, a predetermined low power, and a light wavelength of approximately 300 nanometers to approximately 1200 nanometers, using a controller coupled to the light source, a light from the light source for a predetermined period of time or a period of time based on a feedback from at least one of the following: a trigeminal evoked response data, and an electroencephalogram data, to stimulate the neuronal cell to treat the symptom of the headache-related medical condition; the predetermined frequency includes at least one of the following: a range of 10 cycles per second (Hz) to 20 cycles per second (Hz), and a frequency of less than 1 cycle per second (Hz);
controlling, using the controller, an output of the light source based on at least one of the following in combination with a predetermined output of light: an evoked response of the patient, a trigeminal nerve evoked response, the electroencephalogram, and any combination thereof;
wherein the stimulating including changing at least one property of at least one function of the neuronal cell, wherein the changing of the at least one property includes at least one of the following: quenching the neuronal cell, kindling the neuronal cell, affecting homeostatic information transmission, and any combination thereof;
stopping the stimulating after a predetermined period of time or based on at least one of the following: the evoked response of the patient, the trigeminal nerve evoked response, the electroencephalogram, and any combination thereof.

29. The method according to claim 1, wherein proximate positioning of the light source is performed using at least one of the following: a tip of the light source, a fiber optic head connected to the light source, a fiber optic cable connected to the light source, a fiber optic extension connected to the light source, and any combination thereof.

30. The method according to claim 1, wherein the predetermined time is between 30 seconds and 10 minutes.

31. The method according to claim 1, wherein the proximate positioning includes threading the light source past an inferior turbinate.

32. The method according to claim 1, wherein the proximate positioning includes positioning the light source at a superior turbinate.

* * * * *